(12) United States Patent  
Wright

(10) Patent No.: US 8,048,255 B2
(45) Date of Patent: Nov. 1, 2011

(54) HEATSET ANNULOPLASTY SUTURE GUIDE

(75) Inventor: John T. M. Wright, Denver, CO (US)

(73) Assignee: Medtronic, Inc., Minneapolis, MN (US)

( * ) Notice: Subject to any disclaimer, the term of this patent is extended or adjusted under 35 U.S.C. 154(b) by 692 days.

(21) Appl. No.: 11/627,838

(22) Filed: Jan. 26, 2007

(65) Prior Publication Data

US 2007/0179603 A1  Aug. 2, 2007

Related U.S. Application Data

(60) Provisional application No. 60/763,005, filed on Jan. 27, 2006.

(51) Int. Cl.
*B29C 65/00* (2006.01)
(52) U.S. Cl. ............... 156/304.6; 156/304.1; 156/304.2; 623/2.1; 623/2.36; 623/2.38; 623/2.41
(58) Field of Classification Search ........ 623/2.36–2.41, 623/2.1; 156/304.1, 304.2
See application file for complete search history.

(56) References Cited

U.S. PATENT DOCUMENTS

| 5,674,279 | A | 10/1997 | Wright |
| 2006/0272751 | A1* | 12/2006 | Kato ............................. 148/540 |
| 2007/0067028 | A1 | 3/2007 | Wright |

OTHER PUBLICATIONS

Bex and Lecompte (1986) J. Cardiac Surg., 1:151-159, "Tricuspid Valve Repair Using a Flexible Linear Reducer".

* cited by examiner

*Primary Examiner* — Yogendra Gupta
*Assistant Examiner* — John Robitaille

(57) ABSTRACT

An implantable annuloplasty suture guide is intended to lie against at least a portion of an annulus surrounding a human heart. The implantable annuloplasty suture guide is made of an elongated ribbon of braided, heat setable material. The braided, heat-setable material is heat-set in a curved lengthwise configuration corresponding to at least a portion of the annulus of the human heart valve. A method of making an implantable annuloplasty suture guide configured to lie against at least a portion of an annulus defined by tissue surrounding a human heart. The method includes the steps of providing an elongate biocompatible ribbon comprising a braided, heat setable material. A fixture is provided, with the fixture comprising a heat conducting material defining an elongate cavity having a curved length-wise configuration corresponding to at least a portion of the annulus defined by the tissue surrounding the human heart. The elongate biocompatible ribbon is placed in the cavity and the fixture is heated to provide a select temperature for a select time in the cavity, the select temperature and the select time being sufficient to heat-set the elongate biocompatible ribbon in the curved length-wise configuration.

8 Claims, 8 Drawing Sheets

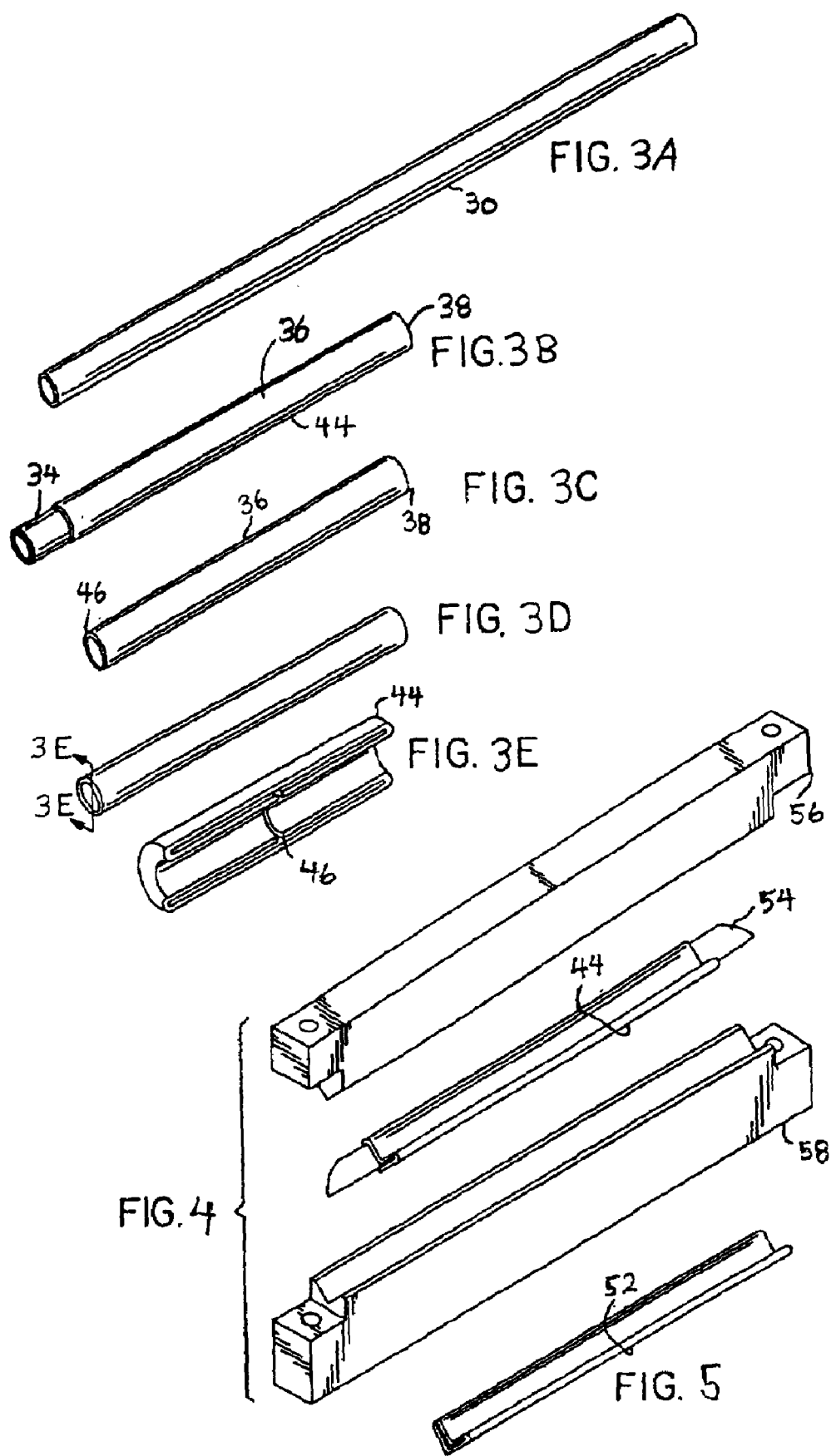

HEATSET ANNULOPLASTY SUTURE GUIDE

RELATED APPLICATIONS

This application claims priority from U.S. Provisional Patent Application Ser. No. 60/763,005, filed Jan. 27, 2006, entitled "Heatset Annuloplasty Suture Guide," which is hereby incorporated by reference.

TECHNICAL FIELD

The present invention is directed toward suture guides, and more particularly toward heatset annuloplasty suture guides and a method of making the same.

BACKGROUND OF THE INVENTION

It is well known in the art to use implantable annuloplasty suture guides for surgical correction of certain mitral or tricuspid heart valve disorders. The heart has two atrio-ventricular valves. The mitral valve is on the left side of the heart and the tricuspid valve is on the right side of the heart. Both valves are subject to damage that requires the valves to be repaired or replaced. Clinical experience has shown that repair of the valve, where this technique is possible, produces better long term results than does valve replacement. The mitral and tricuspid valves differ significantly in anatomy. The annulus of the mitral valve is somewhat D-shaped and the annulus of the triscupid valve is more nearly circular.

Wright et al, U.S. Pat. No. 5,674,279, the contents of which are expressly incorporated by reference herein, describes in detail various effects of valvular dysfunction, known corrective procedures and various prostheses that have been used in conjunction with mitral or tricuspid valve repair. Wright is also directed to an annuloplasty and suture ring structure that has experienced considerable success in mitral and tricuspid valve repair.

Known prosthethis are either completely flexible or have an internal frame in at least a portion of the annuloplasty ring to impart some structural integrity. Those annuloplasty rings having an internal frame can be difficult to install if there is even slight deviation in patient anatomy in the vicinity of an annulus defined by tissue surrounding a human heart valve. Thus, this is one limitation on Carpenter et al. D-shaped closed rings discussed on the Wright '279 patent. Other rings are flexible, such as the Cosgrove-Edwards band which is a fully flexible C-shaped ring and the Metronic Duran ring which is fully flexible and circular. Both of these rings are also discussed in the Wright '279 patent. Because flexible annuloplasty rings can be hard for surgeons to manipulate and install due to their flexible nature, flexible rings typically require a holder for installation by a surgeon. However, fully attaching flexible annuloplasty rings to the circumference of a holder can present difficulties that require relatively tight tolerances between the annuloplasty rings and a holder and the connection process can drive up costs. In addition, known flexible suture rings require attachment of the entire inner circumferential surface of the annuloplasty ring to the holder, which can make it difficult to view the surgical field in the vicinity of a valve annulus and can inhibit access to all portions of the annuloplasty ring.

The present invention is directed toward overcoming one or more of the problems discussed above.

SUMMARY OF THE INVENTION

A first aspect of the present invention is an implantable annuloplasty suture guide intended to lie against at least a portion of an annulus surrounding a human heart valve. The implantable annuloplasty suture heart guide comprises an elongated ribbon of braided, heat setable material. The braided, heat-setable material is heat-set in a curved lengthwise configuration corresponding to at least a portion of the annulus of the human heart valve. The braided, heat-setable material may be a polyethertetraphylate tubular material. The curved lengthwise configuration may be annular D-shaped, substantially circular or a substantially C-shaped. In one embodiment, no internal frame is provided in the braided heat setable tubular material.

The braided, heat-setable material may be a single length of tubular braid material invaginated to form a double walltubed having first and second ends and inner and outer walls. A rollover fold is formed at one end and two cut ends are formed at the other end. The inner and outer walls of the tube are sealed together at the two cut ends to form a seal line. The seal line is rolled to reside substantially centrally in the inner wall of the tube. The tube is formed to define a V cross-section providing an eight walled member and that the eight wall member is heatset to retain the cross-section. In this embodiment, the apices of the V may be joined to form an essentially oval cross-section. Opposing ends of the tube of this embodiment may be joined to form an annular member.

Another aspect of the invention is a method of making an implantable annuloplasty suture guide. The suture guide is configured to lie against at least a portion of an annulus defined by tissue surrounding a human heart. The method includes the steps of providing an elongate biocompatible ribbon comprising a braided, heat-setable material. A fixture is provided, with a fixture comprising a heat conducting material defining an elongate cavity having a curved length-wise configuration corresponding to at least a portion of the annulus defined by the tissue surrounding the human heart valve. The elongate biocompatible ribbon is placed in the cavity and the fixture is heated to provide a select temperature for a select time in the cavity, the select temperature and the select time being sufficient to heatset the elongate biocompatible ribbon in the curved length-wise configuration. The curved lengthwise configuration may be an annular D-shape, substantially circular or a curved segment. The heat-setable material may be a polyetherate tubular material.

In one embodiment, the method further includes the elongate biocompatible ribbon being substantially linear in shape and having opposing first and second ends. Prior to placing the elongate biocompatible ribbon in the cavity, the opposing first and second ends are tied together with a cord extending there between so that the biocompatible ribbon has a C-shape lengthwise configuration. Following heat setting of the biocompatible ribbon, the cord may be removed.

In all embodiments, the select temperature and the select time are preferably such that substantially no degradation of the braided, heat-sedable material occurs during heat setting.

The method may further include forming the braided, heatsetable material into a non-heatset annular configuration by a process which includes providing a single length of tubular braid material and invaginating the single length of tubular braid material to form a double walled tube having first and second ends and inner and outer walls, with a rollover fold formed at one end and two cut ends formed at the other end. The inner and outer walls of the tube are sealed together at the two cut ends to form a seal line. The tube is rolled to place the seal line substantially centrally in the inner wall of the tube. The tube is then formed to define a V cross-section providing an eight wall member. The eight-walled member is then heatset to retain the V cross-section. This embodiment may further include joining the apices of the V to form and essentially oval cross-section. This embodiment may further include attaching opposing ends of the tubes after joining the apices to form a tubular member.

The implantable annuloplasty suture guide of the present invention maintains its basic configuration without the rigidity of the internal frame suture guides such as Carpenter et al. guides. In addition, the said annuloplasty guide has sufficient structural integrity to allow it to be used with a holder providing radially spaced support for the suture guide as opposed to support over the entire circumference of the suture guide. This both makes it easier to attach the suture guide to the holder and allows more access to the suture guide during installation of the suture guide in a heart valve annulus.

Other advantages of the invention will be apparent from the description of the invention as follows and from the appended claims.

BRIEF DESCRIPTION OF THE DRAWINGS

FIGS. 3A-3E are perspective views depicting progressive steps in the formation of an invaginated braided tube used in forming a heatset annuloplasty suture guide;

FIG. 4 is an exploded perspective view of a jig for heat setting the invaginated tube into a V configuration;

FIG. 5 is a perspective view of the heatset V-shaped invaginated tube before having the apices of the V attached to define an eight layer tube;

DETAILED DESCRIPTION OF THE INVENTION

Figure 1:
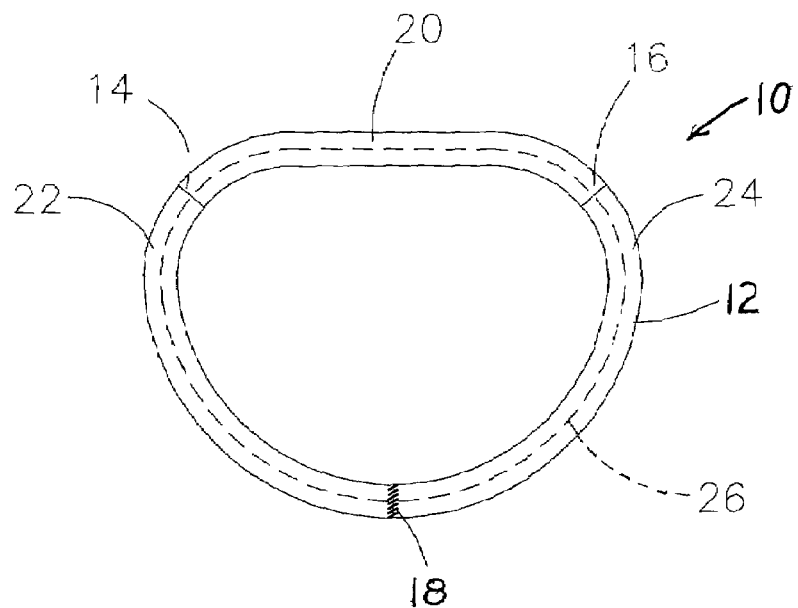
FIG. 1 is a plan view of a heatset annuloplasty suture guide in accordance with the present invention.

A D-shaped heatset annuloplasty suture guide 10 for use in valve repair is shown in a plan view in FIG. 1. The D-shaped annuloplasty suture guide 10 consists of a elongate braided ribbon body 12 made of a heat settable material that has been heatset to a curved lengthwise configuration, in this case a D-shape corresponding to an annulus of a mitral valve in a human heart. The D-shaped annuloplasty suture guide includes colored trigon markers 14, 16 corresponding to the left and right fibrous trigon the mitral valve. The elongate braided ribbon body 12 has its ends sewn together at the seam 18 to form a ring. The ring has three segments, an anterior segment 20, a right posterior segment 22 and a left posterior segment 24. In one embodiment, the braided heat setable ribbon body 12 is tubular and a radio opaque marker indicated in ghost lines at 26 resides within the tube.

The braided heat setable ribbon is made a biocompatible cloth, for example, a tubular braided polyethertetraphylate material. In such an embodiment, during construction of the suture guide, a tubular braided material is cut to length and invaginated to form a double walled tube having a roll overfold at one end, and the two cut ends at the other. The two walls of the tube are heat sealed (welded) together close to the two cut ends an appropriate distance from the folded end using a heated knife. This heat seal forms a circumferential weld around the tube. The tube is then rolled so that the weld line will lie substantially centrally in the inner wall of the tube. The tube is then heatset into a V cross-sectional configuration. This configuration results in an eight-walled flexible construction when the annuloplasty guide is completed. One step in the completion of the annuloplasty guide is sewing of the apices of the V together to form a circumferential seam. A radio opaque marker may be placed within the V form before the circumferential seam is completed.

Another step, used when an annular lengthwise configuration of the braided, heat setable ribbon is desired, is sewing together of the opposing ends forming a radial seam (18 in FIG. 1). The construction described above provides an elongate biocompatible ribbon comprising a braided, heat setable material used in making heatset annuloplasty suture guides that is relatively simple to manufacture, yet which may contain a radio opaque marker for post-operative assessment. It further provides annuloplasty suture guide which, once heatset, provides adequate strength and rigidity while permitting a low needle penetration force for convenient implantation. A particular advantage of this construction is that no portion of the textile material that might fray is exposed and the weld line is placed within the ring where it is inconspicuous and not subject to undue stress. The body resulting from this construction is substantially oval in cross-section, are viewed in FIG. 6.

Figure 2A:
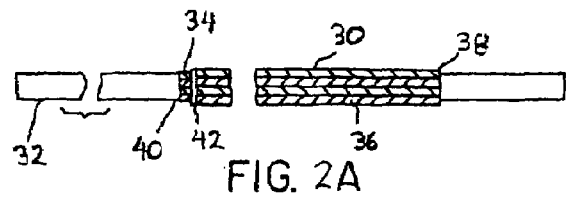
FIGS. 2A-2E are elevation views depicting progressive steps in the formation of an invaginated braided tube used in forming a heatset annuloplasty suture guide.

The initial steps in manufacturing the braided, heat setable biocompatible ribbon 12 outlined above is illustrated in FIGS. 2A-E. A pre-washed length of heat-setable, meltable braided fiber tubing 30, e.g. Atkins & Pearce braided polyester tape, is cut to a desired length, e.g. 250-290 mm, and the cut length is slid over a mandrel 32. The tubing is then rolled back onto the mandrel 32 so as to form a double walled tube, having an inner wall 34 and an outer wall 36, approximately half the length of the original tubing. The tube has an inward fold 38 from the outer wall 36 to the inner wall 34 forming one end, the right end as depicted in FIG. 2A. The other ends of the tubing, 40, 42 lie generally adjacent to one another.

Figure 2B:
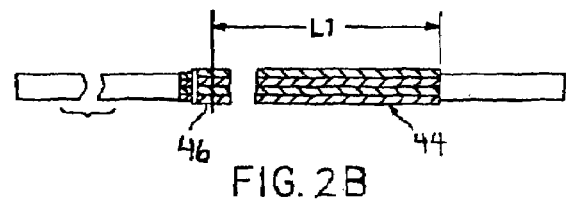

Referring to FIG. 2B, the double walled tube 44 is cut to a desired length, e.g. 112-133 mm, at 46 with a heated blade that cuts by melting the fibers and fusing the fibers together to form a fused end, the inner and outer walls being joined in an annular fused joint at 46.

Figure 2C:
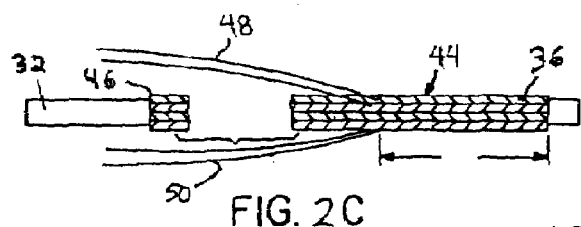
Figure 2D:
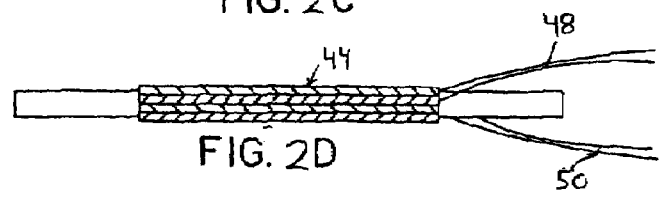
Figure 2E:
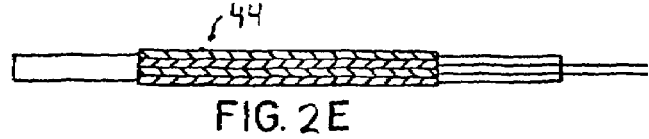

Referring to FIG. 2C, temporary sutures 48, 50 are secured only through the outer layer 6 a desired distance, e.g. 56-66 mm from the end of the tube. The fused joint 46 is then rolled into the inside of the tube so as to turn a portion of the tube inside out, the temporary sutures being used to pull the layer through which they extend to roll the tube inside out to position the fused joint in the inside wall, for example, in the center of the inside wall of the tube 44. To clarify, the tube as shown in FIG. 2B, is rolled inside out so that the sealed-cut ends are on the right as shown in FIG. 2C, the sutures are attached, and the tube is further rolled partially inside out until the sutures are at the right end as shown in FIG. 2D with the heat-sealed joint between the original ends of the tubing inside the final 2-layer tube as shown in FIG. 2B.

The steps in forming the final tube are depicted without the mandrel 32 in FIGS. 3A-E, which also depict the steps of forming the braided, heat setable tubular ribbon. In the first step, a tube of braided, meltable, heat setable polymer fibers 30 is provided and the tube is invaginated to form double-walled layer of tubing 44 having an outer layer of tubing 36 with a first end of the tube being formed to define an annular, inward fold 38 and the outer layer to the inner layer and forming a second end 42 which is cut at 46 by melting the inner and outer layers of the tubing to fuse the layers together in an annular seal between the layers. FIGS. 3D to 3E then illustrate the position of the cut 46 being slid within the interior of the tube.

A double walled tube made in the manner described above may be used in the devices of this invention as a suture guide for heart valves and in any other device or method where a fabric suture guide, ribbon or ring is used to secure a prosthesis to tissue or to secure tissue to tissue.

Referring to FIGS. 4 and 5, a method used in making the braided heat setable ribbon in one advantageous embodiment is further described. This embodiment further includes heat setting the double walled tube 44 into a V-shaped cross-section band 52, having a center heatset crease comprising four layers of tubing.

Figure 6:
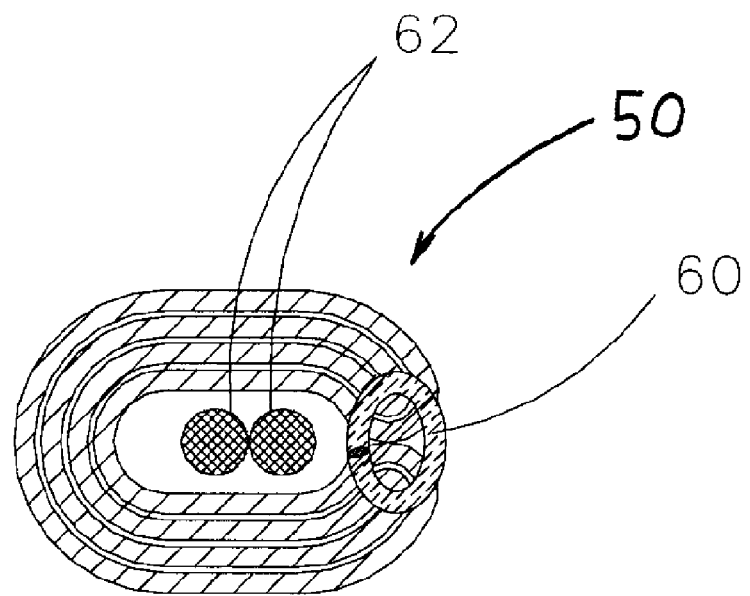
FIG. 6 is a cross-sectional view of an eight layer tube used in making a heatset annuloplasty suture guide.
Figure 7:
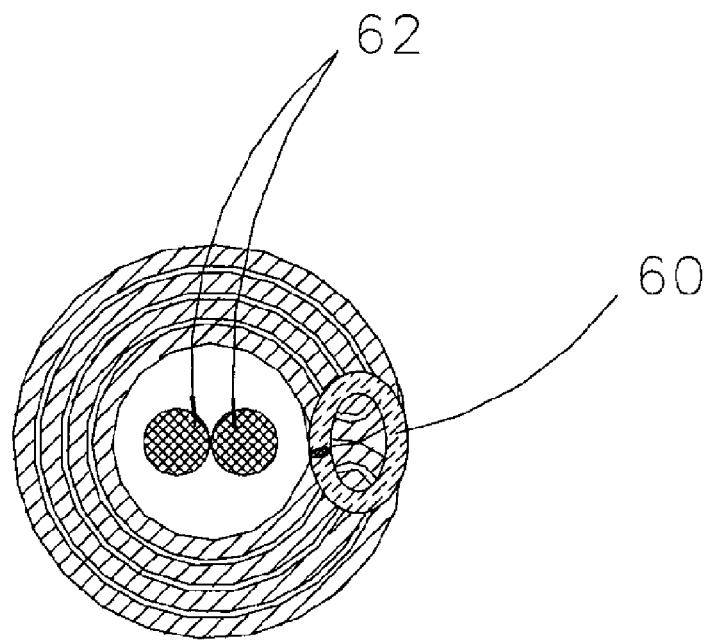
FIG. 7 is a cross-sectional view of a heatset annuloplasty suture guide taken along line 7-7 of FIG. 1.

Reference is made specifically to FIG. 4, which depicts an exploded view of a jig for heat setting the tubing 44 into a V-shaped cross-section band 52. The double-walled tube 44 is slipped over a V-shaped mandrel 54 which may be made of metal or high temperature resistant polymer, e.g. polytetrafluoroethylene. The mandrel 54 carrying the tube 44 is clamped between forming tools 56 and 58 which define a V-shaped opening the size and shape of the desired V-shaped band. A pair of bolts, C clamps, or any other clamping device may be used to secure the forming tools together. Bolts are preferred to maintain alignment of the tools. The clamped tools with the mandrel and tube are placed in an oven, or otherwise heated, to a temperature sufficient to heatset the polymer of which the tubing is formed without fusing it. In the case of polyester, temperatures in the range of 100°-110° C. are quite suitable in most instances. After a sufficient period, usually about 10.5-11 minutes to heat form the tubing, the clamped mandrel, with the tube in place, is first cooled to set the tube into a V-shaped band or ribbon 52 and then removed. The V-shaped band is then formed into a tube 59 by sewing the apices of the V together forming a circumferential seam 60 seen in FIG. 6. Prior to formation of the circumferential seam 60, it may be desirable to insert a radio opaque marker or markers 62 at the valley of the V. The radio opaque marker 62 may be composed of a single or multitude continuous lengths of 0.02 inch diameter extruded silicon rubber impregnated with 55% Barium Sulfate and 6% Tungsten. Two lengths are illustrated in FIGS. 6 and 7. The material of this composition and diameter is sufficiently radio opaque, but does not unduly impede the passage of the needles of the implanting sutures. As further illustrated in FIG. 6, the fully formed elongate biocompatible ribbon consists of eight layers of material. FIG. 7 illustrates a cross-section of the biocompatible ribbon after is has been heatset in a select curved length-wise configuration as described in detail below and demonstrates how the cross-section goes from substantially elliptical in FIG. 6 to substantially circular FIG. 7.

Figure 8:
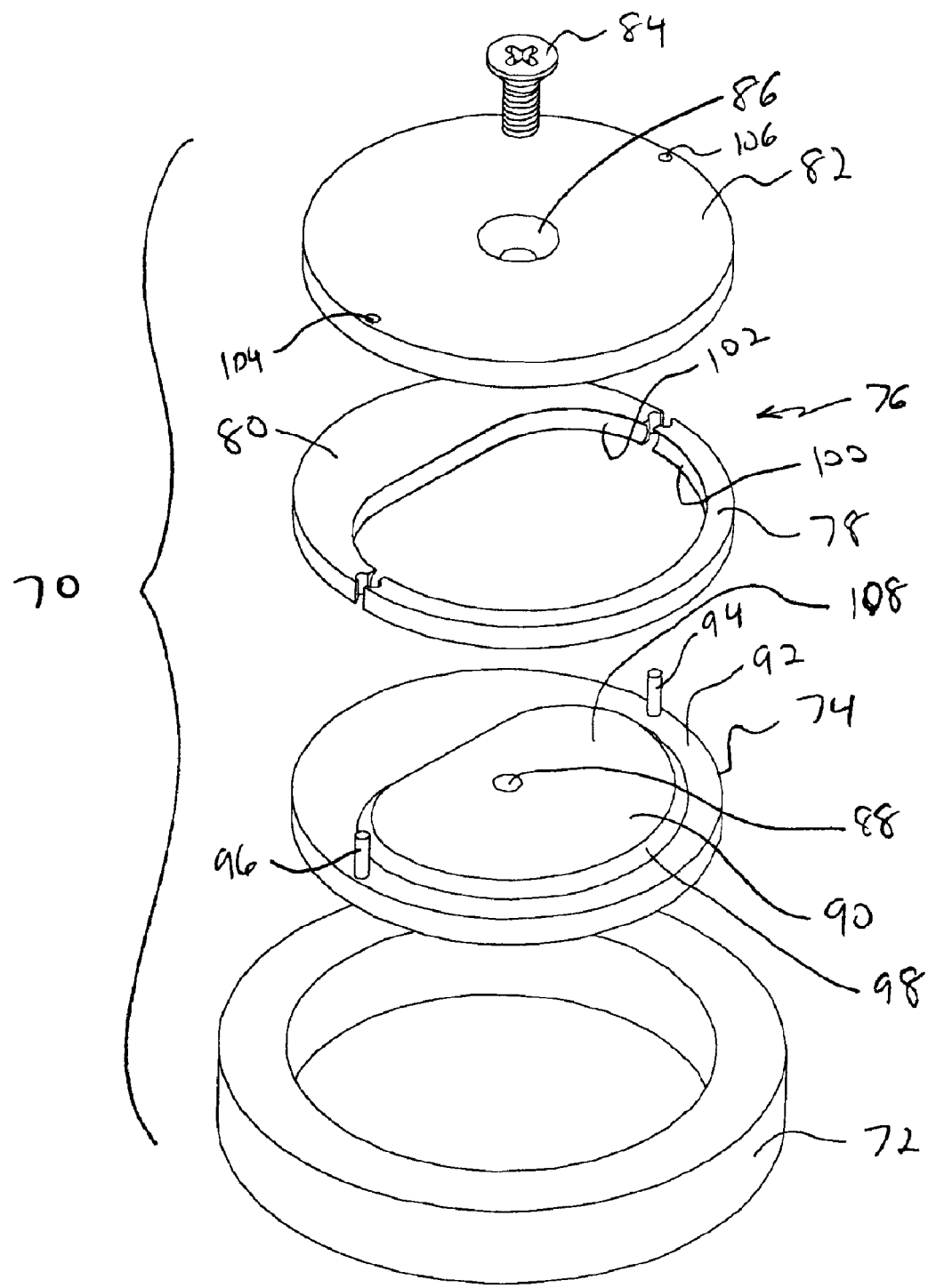
FIG. 8 is a perspective exploded view of the elements of a heatset fixture.

FIG. 8 an exploded perspective view of a fixture 70 for forming elongate biocompatible ribbon, such as the ribbon 59 of FIG. 6, to a curved length-wise configuration corresponding to at least a portion of the annulus defined by tissue surrounding a human heart valve. The fixture 70 consists of an outer ring 72, a base member 74, an annular insert 76 (comprising a semicircular half 78 and a D-shaped half 80) and a cap 82. A screw 84 is received within a hole 86 in the cap 82 for threaded engagement with threaded hole 88 the base member 74.

In the embodiment of the fixture 70 illustrated in FIG. 8, the base member 74 has a D-shaped platform 90 extending from planar principal surface 92. Alignment posts 94, 96 also extend axially from the planar principal surface 92. A circumferential edge 98 of the D-shaped platform 90 has a concave cross-section (see FIG. 10) corresponding to roughly 90 degrees of a circular radius.

The semi circular half 78 of the annular insert 76 has an inner circumferential edge 100 that also has a concave cross-section. In this instance, the concave cross-section extends about a radius of over 90 degrees. Likewise, the D-shaped half 80 has an inner circumferential edge 102 having a concave cross-section corresponding to that of the inner circumferential edge 100 of the semicircular half 78.

The fixture 70 is assembled by mating the semi-circular half 78 and the D-shaped half 80 of the annular insert 76 with the alignment posts 94, 96 of the base member 74. Alignment holes 104, 106 of the cap 82 are likewise aligned with the alignment posts 94, 96 to sandwich the annular insert 76 between the cap 82 and the base member 74. Screw 84 is then received in the hole 86 (which is preferably counter sunk to receive the V-shaped head of the screw 84) and the threaded shaft of the screw threably engages the threaded hole 88 to hold the pieces in their sandwiched configuration. The sandwich is then received in the central hole of the outer ring 72.

Figure 9:
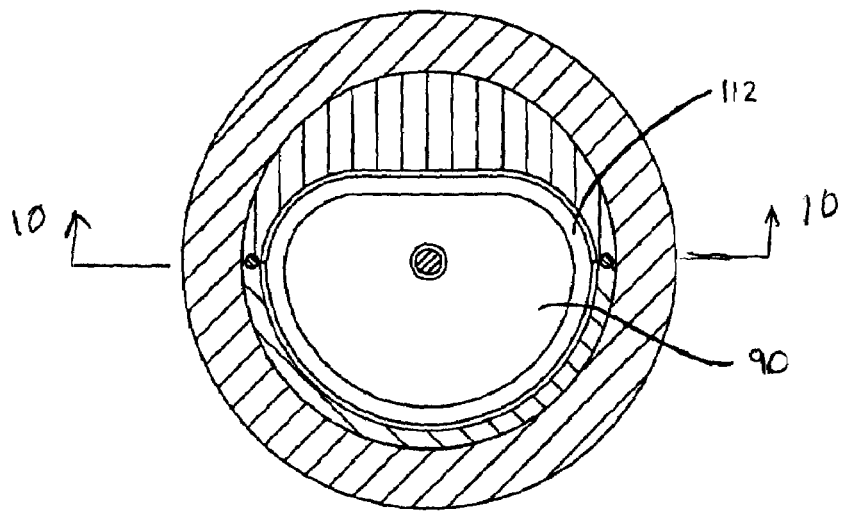
FIG. 9 is a plan cross-sectional view of the assembled heatset fixture.
Figure 10:
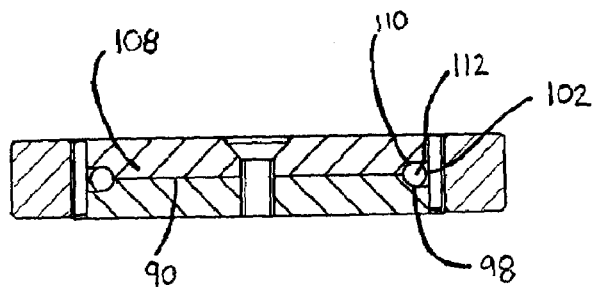
FIG. 10 is an elevational cross-sectional view of the assembled heatset fixture taken along line 10-10 of FIG. 9.

Referring to FIG. 10, a platform 108 also extends axially from a bottom surface of the cap 82. The platform 108 has a concave circumferential edge 110 corresponding to the circumferential edge 98 of the platform 90. With opposing planar surfaces of the platforms 90, 108 abutted as illustrated in FIG. 10, the elongate cavity 112 has a curved length-wise configuration corresponding to at least a portion of a lengthwise configuration annulus defined by tissue surrounding a valve of a human heart (see FIG. 9). Referring again to FIG. 10, the cavity 112 is defined by the concave circumferential edge 98 of the platform 90, the concave circumferential edge 110 of the platform 108 and the concave inner circumferential edge 100 of the semi-circular half 78 or the concave inner circumferential edge 102 of the D-shaped half 80. As seen in FIG. 10, the cavity 112 has essentially a circular cross-section. Referring to FIG. 9, which is a cross-section taken at about a plane corresponding to the planar surface of the platform 90, this embodiment of the fixture 70 provides a D-shaped length-wise configuration in the elongate cavity.

Figure 11:
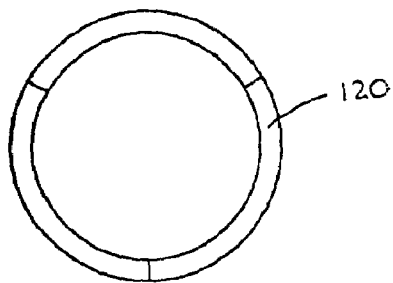
FIG. 11 is a plan view of a non-heatset braided tubular annuloplasty suture guide formed into a ring.
Figure 12:
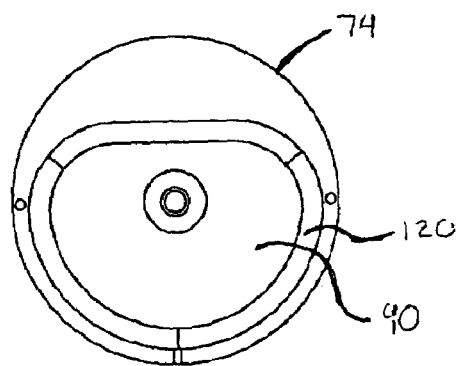
FIG. 12 is a plan view of the non-heatset braided annuloplasty ring of FIG. 11 placed on a circumferencial edge of a fixture platform.
Figure 13:
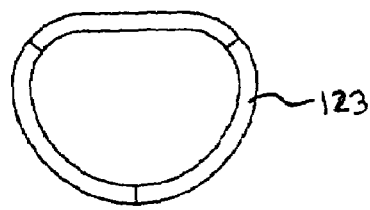
FIG. 13 is a plan view of a heatset D-shaped annuloplasty suture guide.

FIG. 11 is a plan view of a heat setable braided tubular biocompatible ribbon formed into a ring 120. The heat setable braided tubular biocompatible ribbon formed into a ring 120 of FIG. 11 is preferably constructed in the manner discussed above with reference to FIGS. 1-7. In forming a D-shaped heatset annuloplasty suture guide, the heat setable tubular biocompatible ribbon 120 is conformed to the concave circumferential edge 98 of the platform 90 of the base 74 as illustrated in FIG. 12. The remaining parts of the fixture are then assembled as explained above with the heat setable braided tubular biocompatible ribbon closed in the elongate cavity 112 as illustrated in FIGS. 9 and 10. The elements of the fixture 70 are made of a heat conductive material, for example, anodize aluminum. The assembled fixture is then heated to provide a temperature of between about 100° and 110° Celsius in the cavity for a period of about 10.5-11 minutes to heatset the braided tubular biocompatible ribbon 12 into a D-shaped suture guide configuration 123 as illustrated in FIG. 13. Heat setting the suture guide at this temperature and this time period does not substantially degrade the braided, heat-setable material and allows it to readily receive a needle while being sutured to a heart valve annulus.

Figure 14:
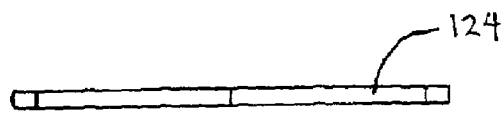
FIG. 14 is a non-heatset elongate annuloplasty suture guide.
Figure 15:
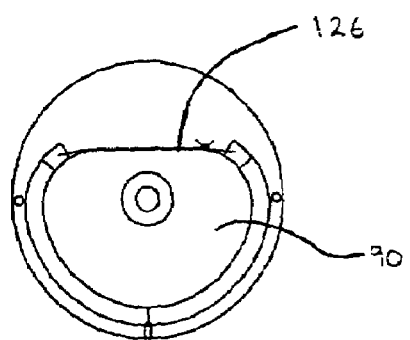
FIG. 15 is the non-heatset elongate annuloplasty suture guide of FIG. 14 with its end attached by a cord placed a circumferential edge of a fixture platform.
Figure 16:
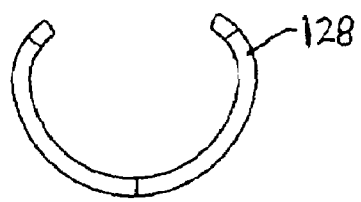
FIG. 16 is a heatset annuloplasty suture guide of FIG. 15 following removal of the cord.

FIG. 14 illustrates a linear heat setable braided biocompatible ribbon 124. As with the ring shaped embodiment 120, the linear embodiment 124 is preferably formed in the manner discussed above with regards to FIGS. 1-7. A cord 126 is secured between the ends of the linear heat setable braided biocompatible ribbon 124 as illustrated in FIG. 15 and the linear heat setable braided biocompatible ribbon 124 is fit about the platform 90 as illustrated in FIG. 15. The fixture is then assembled as described above and the linear heat setable braided biocompatible ribbon 124 is heatset into a C-shaped configuration annuloplasty guide 128 illustrated in FIG. 16.

As will be appreciate by one of skill in the art, the platforms 90-108 are not limited to D-shaped circumferential configurations but may be circular when, for example, forming a tricuspid annuloplasty suture guide. Other lengthwise configurations can also be selected to conform to other annulus cross sections to form suture guides of varying length-wise configurations other than circular, D and C lengthwise configurations. One result of the substantially circular cross-section of the elongate cavity 112 is that upon heat setting, the substantially elliptical cross-section of the tube in FIG. 6 becomes substantially circular as illustrated in FIG. 7.

Suture guides heatset in a select curved length-wise configuration in accordance with the method described above will retain their shape in post-forming detergent washing, rinsing and drying. In addition, the heatset annuloplasty suture guides retain their configuration while being implanted, thereby making them easier for a surgeon to manipulate and providing a closer match to the anatomical features of, for example, a heart valve annulus.

Figure 17:
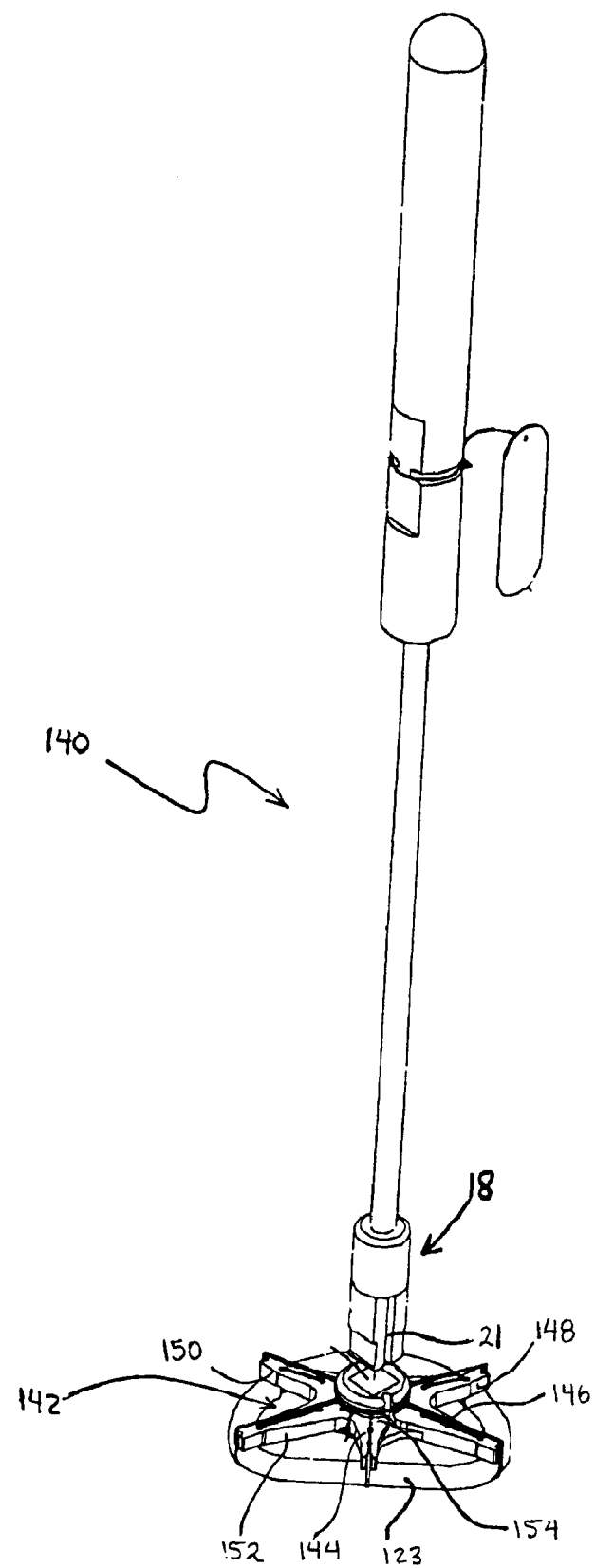
FIG. 17 is a perspective view of an annuloplasty suture guide holder with an annuloplasty suture guide having a D-shaped configuration attached thereto.

FIG. 17 is a perspective view of an annuloplasty suture guide holder 140 having a D-shaped heatset annuloplasty guide 123 attached thereto. The annuloplasty suture guide holder 140 is described in greater detail in U.S. provisional application No. 60/719,483, filed Sep. 21, 2005 and U.S. patent application Ser. No. 11/534,188 filed Sep. 21, 2006, now issued as U.S. Pat. No. 7,691,143, the disclosures of which are incorporated in their entirety herein. For the present discussion, the relevant portion of the annuloplasty suture guide 140 is the holder head 142 which consists of a number of spokes 144, 46, 148, 150, 152 radiating from a central hub 154. The various spokes 144-152 radiate a length such that D-shaped annuloplasty suture guide 123 conforms to the distal end of the underside of the spokes. Because the D-shaped annuloplasty suture guide is heatset, it can be easily tied by a suture to the head 142 as illustrated in FIG. 17. When the heatset D-shaped annuloplasty guide 123 is then implanted surgically, the gaps between the spokes provide a viewing area for the surgeon and also allow access to the back side and inner circumference of the suture guide.

Figure 18:
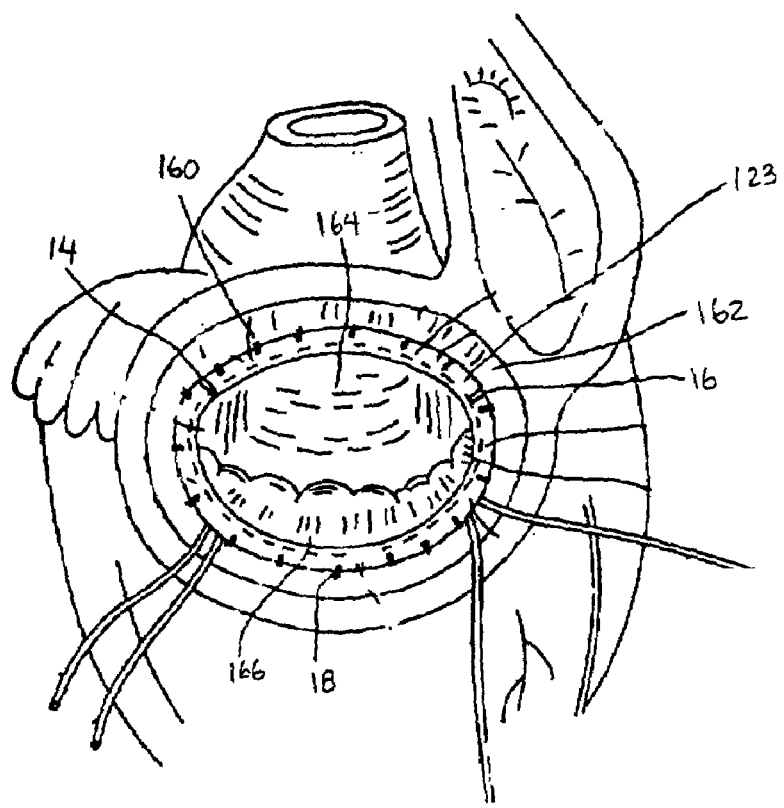
FIG. 18 is an isometric view of an annuloplasty suture guide for mitral valve repair sewn into the mitral annulus of a heart.

FIG. 18 shows an isometric view of the D-shaped annuloplasty guide 123 for mitral valve repair attached to the mitral annulus of a heart (the left atrium is removed for clarity of illustration). The heart is shown during ventricular systole (i.e., the mitral valve is closed and the left ventricular outflow track is pressurized). The D-shaped heatset annuloplasty guide 123 is positioned such that colored markers 14, 16 are coincident to the left fibrous trigone 160 and the right fibrous trigone 162 of the mitral valve annulus. The anterior leaflet 164 is shown coapting the posterior leaflet 166. Seam 18 lies approximately at the mid point of the posterior portion of the annulus.

Figure 19:
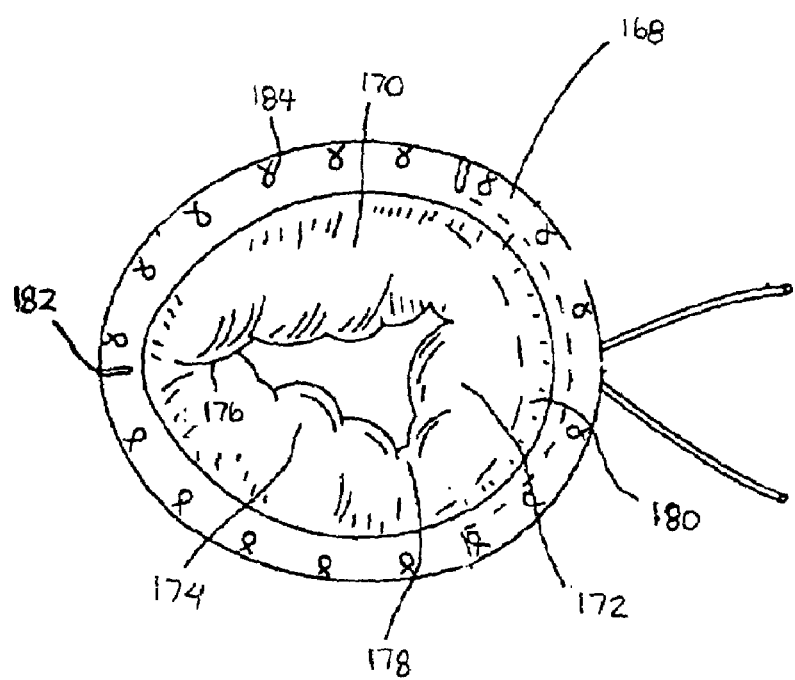
FIG. 19 is a plan view of an annuloplasty suture guide for tricuspid valve repair sewn into an enlarged tricuspid annulus.

FIG. 19 is a plan view of circular-shaped heatset annuloplasty guide 168 for tricuspid valve repair sutured in place in a typically enlarged tricuspid annulus (as described by Bex, J. P., and Lecompte Y. "Tricuspid Valve Repair Using A Flexible Linear Reducer", J. Cardiac Surg., 1:151, 1986). The tricuspid valve has an anterior leaflet 170, a posterior leaflet 172 and a septal leaflet 174. The junction of the septal and anterior leaflets is 76 and the junction of the posterior and septal leaflet is marked 178. The dotted line 180 shows the circumference of the annulus before pathologic dilatation. The annuloplasty ring 168 is positioned so that the colored thread 182 approximately coincident with the junction 176. Numerous interrupted sutures 184 are used to fix the annuloplasty ring to the tricuspid valve annulus.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

The invention claimed is:

1. A method of making an implantable annuloplasty suture guide, the annuloplasty suture guide being configured to lie against at least a portion of an
annulus defined by tissue surrounding a human heart valve, the method comprising:
a) providing an elongate biocompatible ribbon comprising a braided, heat settable material;
b) providing a fixture, the fixture comprising a heat conducting material defining an elongate cavity having a curved length-wise configuration corresponding to the at least a portion of the annulus defined by tissue surrounding a human heart valve, whereby the elongate cavity has at least a non-linear lengthwise segment;
c) placing the elongate biocompatible ribbon in the cavity; and
d) eating the fixture to provide a select temperature for a select time in the cavity, the select temperature and the select time being sufficient to heatset the elongate biocompatible ribbon in the curved length-wise configuration.

2. The method of claim 1 wherein the braided, heat setable material is a braided polyethertetraphylate tubular material.

3. The method of claim 1 wherein the curved lengthwise configuration is an annular D-shape.

4. The method of claim 1 wherein no internal frame is provided in the braided polyethertetraphylate tubular material.

5. The method of claim 1 step d) is performed without substantially degrading the braided, heat setable material.

6. The method of claim 1 further comprising prior to step a), forming the braided, heat setable material into an non-heat set annular configuration by a process comprising:
providing a single length of tubular braid material;

invaginating the single length of tubular braid to form a double walled tube having first and second ends and inner and outer walls, with a roll over fold formed at one end and two cut ends formed at the other end;

sealing the inner and outer walls of the tube together at the two cut ends form a seal line;

rolling the tube to place the seal line substantially centrally in the inner wall of the tube;

forming the tube to define a V cross-section providing an eight walled member;

heat setting the eight walled member to retain the V cross-section.

7. The method of claim 6 further comprising:

joining the apecies of the V to form an essentially oval cross-section.

8. The method of claim 7 further comprising following joining of the apices, attaching opposing ends of the tubes to form an annular member.

* * * * *